United States Patent
Jensen et al.

(10) Patent No.: US 11,589,824 B2
(45) Date of Patent: Feb. 28, 2023

(54) SYSTEM AND METHOD FOR ESTIMATING THE BRAIN BLOOD VOLUME AND/OR BRAIN BLOOD FLOW AND/OR DEPTH OF ANESTHESIA OF A PATIENT

(71) Applicant: Quantium Medical SL, Mataro Barcelona (ES)

(72) Inventors: Erik Weber Jensen, Sant Pol de Mar (ES); Carmen Gonzalez Pijuan, Barcelona (ES)

(73) Assignee: Quantium Medical SL, Mataro Barcelona (ES)

( * ) Notice: Subject to any disclaimer, the term of this patent is extended or adjusted under 35 U.S.C. 154(b) by 187 days.

(21) Appl. No.: 16/621,411

(22) PCT Filed: May 29, 2018

(86) PCT No.: PCT/EP2018/064061
§ 371 (c)(1),
(2) Date: Dec. 11, 2019

(87) PCT Pub. No.: WO2018/228813
PCT Pub. Date: Dec. 20, 2018

(65) Prior Publication Data
US 2020/0222008 A1  Jul. 16, 2020

(30) Foreign Application Priority Data
Jun. 14, 2017  (EP) .................................... 17382364

(51) Int. Cl.
*A61B 5/026* (2006.01)
*A61B 5/00* (2006.01)
(Continued)

(52) U.S. Cl.
CPC ............ *A61B 5/7217* (2013.01); *A61B 5/026* (2013.01); *A61B 5/0245* (2013.01); *A61B 5/316* (2021.01);
(Continued)

(58) Field of Classification Search
CPC ....... A61B 5/7217; A61B 5/316; A61B 5/369; A61B 5/0245; A61B 5/026; A61B 5/4821;
(Continued)

(56) References Cited

U.S. PATENT DOCUMENTS

| 3,340,867 A | 9/1967 | Kubicek et al. |
| 3,835,840 A | 9/1974 | Mount |

(Continued)

FOREIGN PATENT DOCUMENTS

| CN | 106730213 | 5/2017 |
| JP | 2002516138 | 6/2002 |

(Continued)

OTHER PUBLICATIONS

Cawley, Robert, and Guan-Hsong Hsu. "Local-geometric-projection method for noise reduction in chaotic maps and flows." Physical review A 46.6 (1992): 3057 (Year: 1992).*
(Continued)

*Primary Examiner* — Andrey Shostak
(74) *Attorney, Agent, or Firm* — Cook Alex Ltd.

(57) ABSTRACT

A system (1) for estimating the brain blood volume and/or brain blood flow and/or depth of anesthesia of a patient, comprises at least one excitation electrode (110E) to be placed on the head (20) of a patient (2) for applying an excitation signal, at least one sensing electrode (110S) to be placed on the head (20) of the patient (2) for sensing a measurement signal caused by the excitation signal, and a processor device (12) for processing said measurement
(Continued)

signal (VC) sensed by the at least one sensing electrode (110S) for determining an output indicative of the brain blood volume and/or the brain blood flow. Herein, the processor device (12) is constituted to reduce noise in the measurement signal (VC) by applying a non-linear noise-reduction algorithm. In this way a system for estimating the brain blood volume and/or the brain blood flow of a patient is provided which may lead to an increased accuracy and hence more exact estimates.

8 Claims, 8 Drawing Sheets

(51) Int. Cl.
| | | |
|---|---|---|
| A61B 5/0245 | (2006.01) | |
| G06F 17/18 | (2006.01) | |
| G06N 3/04 | (2023.01) | |
| G06N 3/08 | (2023.01) | |
| G06N 7/02 | (2006.01) | |
| A61B 5/316 | (2021.01) | |
| A61B 5/369 | (2021.01) | |

(52) U.S. Cl.
CPC ............ *A61B 5/369* (2021.01); *A61B 5/4821* (2013.01); *A61B 5/7225* (2013.01); *A61B 5/7246* (2013.01); *A61B 5/7264* (2013.01); *A61B 5/7275* (2013.01); *G06F 17/18* (2013.01); *G06N 3/0436* (2013.01); *G06N 3/08* (2013.01); *G06N 7/02* (2013.01)

(58) Field of Classification Search
CPC ................ A61B 5/7225; A61B 5/7246; A61B 5/7264; A61B 5/7275; A61B 5/7242; A61B 5/0535; A61B 5/4064; A61B 5/725; A61B 5/374; A61B 5/0295; A61B 5/7239; A61B 5/7267; A61B 5/7203; G06F 17/18; G06N 3/0436; G06N 3/08; G06N 7/02
See application file for complete search history.

(56) References Cited

U.S. PATENT DOCUMENTS

| | | | |
|---|---|---|---|
| 6,406,427 | B1 | 6/2002 | Williams et al. |
| 8,211,031 | B2 | 7/2012 | Poupko et al. |
| 8,277,385 | B2 | 10/2012 | Berka et al. |
| 9,474,452 | B2 | 10/2016 | Kochs et al. |
| 10,285,606 | B2 | 5/2019 | Jensen |
| 2002/0082514 | A1* | 6/2002 | Williams ............ A61B 5/4094 600/544 |
| 2003/0163058 | A1* | 8/2003 | Osypka .............. A61B 5/02007 600/513 |
| 2007/0287899 | A1* | 12/2007 | Poupko ................ A61B 5/0535 600/383 |
| 2010/0268096 | A1* | 10/2010 | Berka .................... A61B 5/374 600/485 |
| 2011/0060201 | A1* | 3/2011 | Marks .................. A61B 5/0535 600/324 |
| 2011/0196245 | A1* | 8/2011 | Poupko ................ A61B 5/4839 600/506 |
| 2014/0155706 | A1* | 6/2014 | Kochs ................ A61B 5/02405 600/301 |
| 2014/0316218 | A1* | 10/2014 | Purdon ................ A61B 5/0075 600/301 |
| 2016/0374581 | A1 | 12/2016 | Jensen |

FOREIGN PATENT DOCUMENTS

| | | |
|---|---|---|
| JP | 2008529708 | 8/2008 |
| JP | 2010512828 | 4/2010 |
| RU | 2585143 C1 | 5/2016 |
| WO | 2017012622 A1 | 1/2017 |

OTHER PUBLICATIONS

International Search Report and Written Opinion for International Application No. PCT/EP2018/064061 dated Sep. 10, 2018.

* cited by examiner

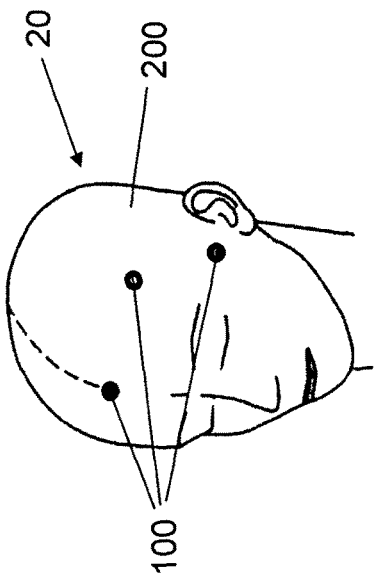
FIG 2
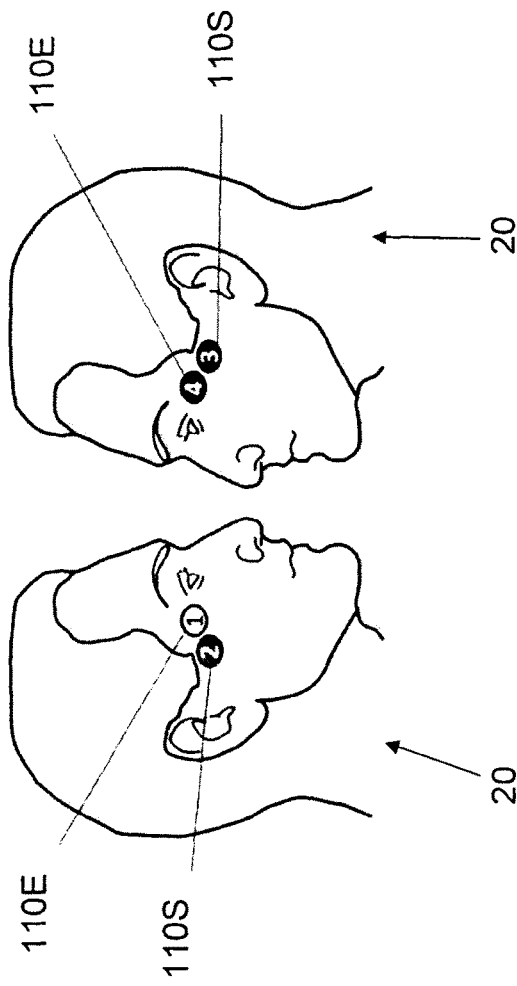
FIG 3A
FIG 3B

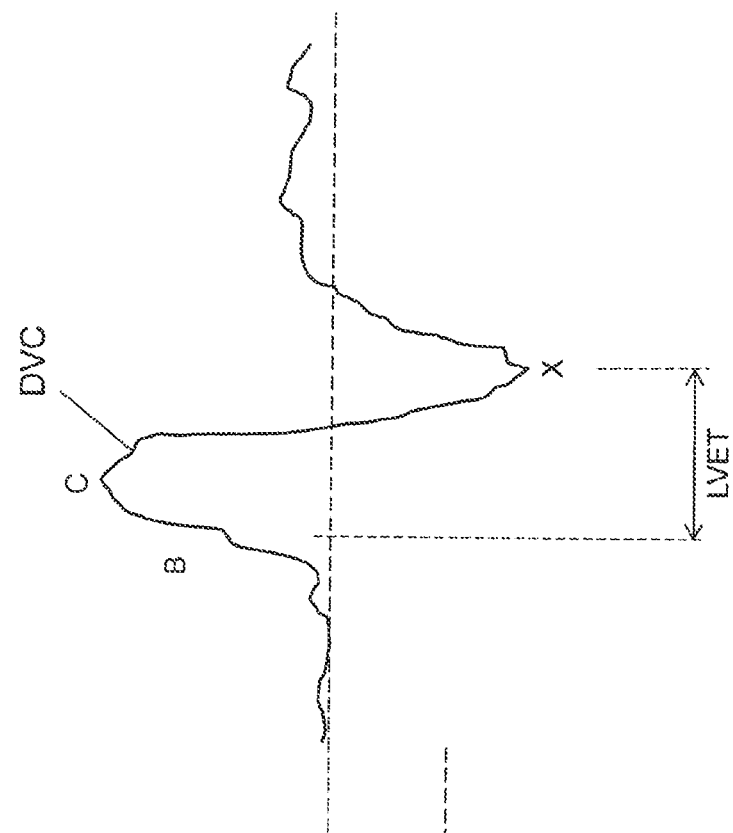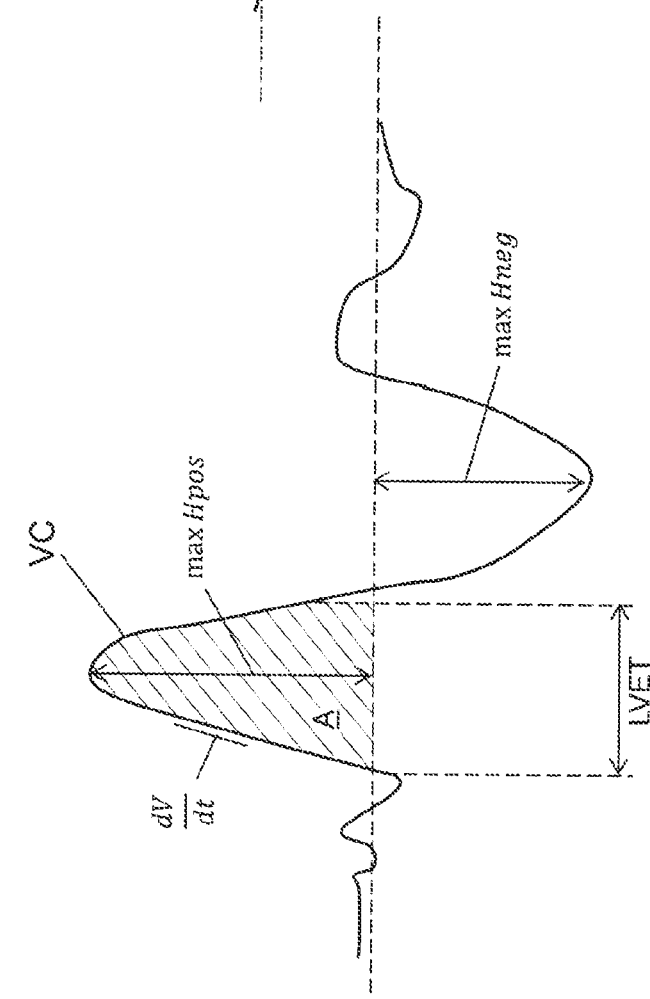

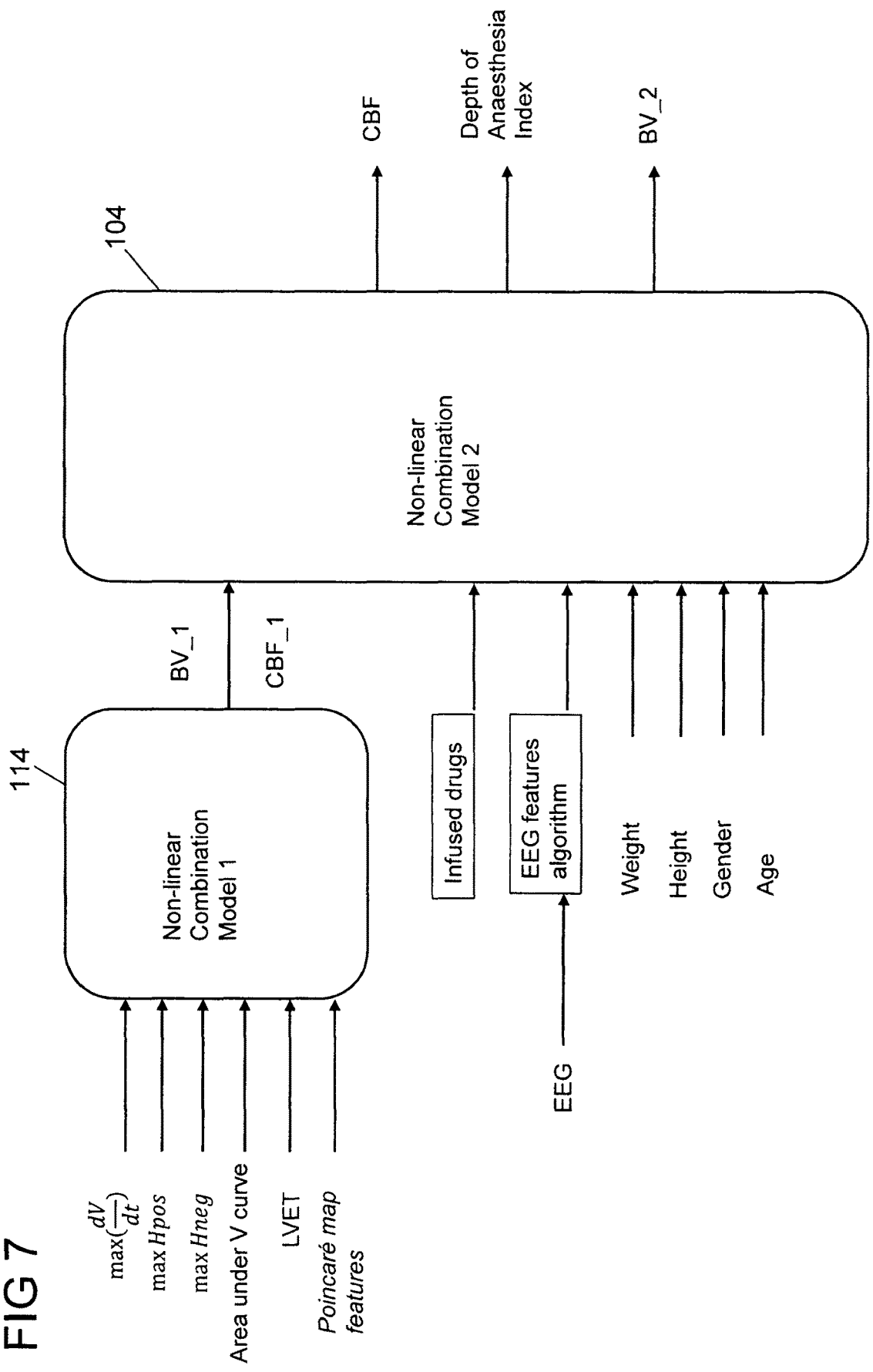

SYSTEM AND METHOD FOR ESTIMATING THE BRAIN BLOOD VOLUME AND/OR BRAIN BLOOD FLOW AND/OR DEPTH OF ANESTHESIA OF A PATIENT

CROSS-REFERENCE TO RELATED APPLICATIONS

The present application is a U.S. National Stage of PCT International Patent Application No. PCT/EP2018/064061, filed May 29, 2018, which claims priority to EP Application No. 17382364, filed Jun. 14, 2017, both of which are hereby incorporated herein by reference.

The invention relates to a system for estimating the brain blood volume and/or brain blood flow and/or depth of anesthesia of a patient according to the preamble of claim 1 and to a method for estimating the brain blood volume and/or brain blood flow of a patient.

A system of this kind comprises at least one excitation electrode to be placed on the head of a patient for applying an excitation signal, and at least one sensing electrode to be placed on the head of the patient for sensing a measurement signal caused by the excitation signal. A processor device serves for processing said measurement signal sensed by the at least one sensing electrode for determining an output indicative of the brain blood volume and/or the brain blood flow.

Generally, patient's haemodynamic status for example during anesthesia may change rapidly, such that a frequent or even continuous monitoring of cerebral blood volume and cerebral blood flow may provide useful information allowing for a rapid reaction when brain perfusion is compromised, including a fast adjustment of anesthetics if needed.

The excitation signal excited by the at least one electrode may for example be an electrical current which is injected at a predetermined frequency and at constant amplitude. For example, an arrangement of multiple excitation electrodes, for example two excitation electrodes, may be placed on the head of the patient to let a current flow from one excitation electrode to the other. By means of one or multiple sensing electrodes, then, a voltage signal can be detected which is linked to the injected excitation current by the bio-impedance of the patient.

The measuring of bio-impedance on body parts is for example described in U.S. Pat. No. 3,340,867, which discloses a so-called impedance plethysmography in particular useful for determining cardiac output.

U.S. Pat. No. 3,835,840 describes an impedance plethysmography apparatus and method for using the electrical impedance as a correlate to blood flow in the aorta or other arteries.

There generally is a desire to be able to provide a rather exact estimate of a brain blood flow and a brain blood volume of a patient, in particular during anesthesia. Hence, when processing a measurement signal it is necessary to remove noise and artifacts such that noise or artifacts do not have a (large) influence on the accuracy of the processing. In this context it can be assumed that in general filtering techniques employing for example low-pass or bandpass filters do not yield a sufficient accuracy because, in particular in the context of bio-impedance measurements, the measurement signal may have a wide-spread, potentially varying frequency spectrum exhibiting different frequency contents, such that conventional filtering techniques may have an undesired effect on the signal itself.

The term "brain blood volume" (or just blood volume) in the context of this text is to be understood to refer to the amount of blood that is affected by the bio-impedance measurement approach using the at least one excitation electrode and the at least one sensing electrode. In particular, it can be assumed that an excitation signal, in particular an injected current, will flow along the path of least resistance (impedance), in particular along blood-filled arteries. Hence, a measured signal correlating to the impedance will be lower the more blood is present, and vice versa. Hence, when using an arrangement comprising two excitation electrodes placed for example on the opposite temples of the patient's head, the brain blood volume indicates the amount of blood present in between the two excitation electrodes and having an influence on the guidance of the excitation signal.

The term "brain blood flow" (or cerebral blood flow, in short CBF) in the context of this text is to be understood as the blood volume per minute that reaches the brain.

WO 2015/086020 A1 describes an apparatus for determining stroke volume, cardiac output and systemic inflammation by a fuzzy logic combination of features extracted from a voltage measured over the thorax, electrocardiogram and electroencephalogram.

It is an object of the instant invention to provide a system and a method for estimating the brain blood volume and/or the brain blood flow of a patient which may lead to an increased accuracy and hence more exact estimates.

This object is achieved by means of a system comprising the features of claim 1.

Accordingly, the processor device is constituted to reduce noise in the measurement signal by applying a non-linear noise-reduction algorithm, in particular using a Poincaré map analysis.

Within a Poincaré map analysis, in particular an attractor may be constructed from a (noise-corrupted) time series representing a measurement signal, points of the attractor may be clustered in so-called neighbourhoods, the neighbourhoods may be projected, and a new time series representing a noise-reduced measurement signal may be reconstructed from the projected neighbourhoods.

The process including the above steps may iteratively be repeated. The algorithm hence may again be applied to the reconstructed signal until a noise reduction considered sufficient for a further processing is obtained.

The non-linear noise-reduction algorithm may in particular include:

determining an m-dimensional Poincaré map from the measurement signal, clustering points according to neighbourhoods in the Poincaré map, defining a coordinate system for each neighbourhood according to the center of gravity of the neighbourhood, determining coordinates of points in the neighbourhoods using the coordinate system of each neighbourhood, differentiating coordinates having a strong contribution to the variance of the measurement signal from coordinates having a reduced contribution to the variance of the measurement signal, and removing coordinates having a reduced contribution to the variance of the measurement signal to obtain a new set of coordinates for each neighbourhood, defining a new coordinate system for each neighbourhood according to the new set of coordinates, the new coordinate system having a reduced number of dimensions, and projecting the points in each neighbourhood into the new coordinate system.

This is based on the finding that, in order to obtain an increased accuracy when processing bio-impedance measurement signals, a noise reduction algorithm may be used which is based on Poincaré map analysis in order to reduce the interferences without introducing any phase shifts in the measurement signal.

A non-linear noise reduction algorithm making use of Poincaré map analysis is for example described by Maria G. Signorini, Fabrizio Marchetti and Sergio Cerutti in "Applying Non-linear Noise Reduction in the analysis of Heart Rate Variability. A promising tool in the Early Identification of Cardiovascular Dynamics", IEEE Engineering in Medicine and Biology Magazine, March/April 2001, pages 59-68, whose contents shall be incorporated by reference herein.

A noise reduction algorithm making use of Poincaré map analysis is also for example described by R. Cawley and G.-H. Hsu in "Local-geometric-projection method for noise reduction in chaotic maps and flows", Physical Review A, Col. 46, No. 6, 1992, pages 3057-3082, whose contents shall be incorporated by reference herein.

The noise reduction algorithm applied by the processor device for example makes use of a Poincaré map analysis. For forming Poincaré maps, the measurement signal, in a digitized form, is plotted over a delayed version of the measurement signal, wherein multidimensional Poincaré maps for different delays are obtained (each delay corresponds to a dimension of the Poincaré map). Within a Poincaré map, points of the measurement signal are clustered according to neighbourhoods, and within the neighbourhoods the coordinates of each point are recalculated by considering the gravity center of the neighbourhood as the new reference. Coordinates which have a strong influence on the variance of the measurement signal are differentiated from coordinates having a reduced contribution to the variance of the measurement signal. The contribution of each particular dimension to the variance of the points in the neighbourhood is computed, and some of those dimensions are eliminated based on the assumption that those coordinates having a reduced contribution to the variance can be expected to be due to noise. Hence, by the Poincaré map analysis a noise-reduced measurement signal is obtained, which can be used for the further processing in order to derive an estimate of the brain blood volume and the brain blood flow.

By removing the number of dimensions in the neighbourhoods, noise is reduced locally for every set of points, preserving the most significant patterns of the points in the vicinity. In this way, the so-called attractor of the measurement signal is used to reconstruct the measurement signal, which now is presumably being little affected by noise.

In one embodiment, the at least one excitation electrode is controlled to inject an electrical current having one or multiple predetermined frequencies and/or having a constant amplitude. Hence, via the at least one excitation electrode a current is injected, which flows through a region of the patient and causes a voltage signal, which can be picked up by the at least one sensing electrode as the measurement signal. The voltage signal, also denoted as the voltage plethysmographic curve, voltage plethysmogram or voltage curve, is linked to the injected current via the bio-impedance, which in particular is influenced by blood flowing through the arteries of the patient's head on which the at least one excitation electrode and the at least one sensing electrode is placed.

The excitation current may for example have a constant amplitude of 50 to 1000 µA and may have a high frequency, for example 50 kHz.

In one embodiment, two excitation electrodes may be placed on the head of the patient, for example one excitation electrode on the left temple and another excitation electrode on the right temple of the head of the patient. The current hence flows in between the two excitation electrodes along the path of least resistance (impedance), i.e., along the blood-filled arteries within the head of the patient. In addition, for example two sensing electrodes may be used, each sensing electrode being placed in the neighbourhood of one excitation electrode on a temple of the patient's head.

In one embodiment, the measurement signal sensed by the at least one sensing electrode is processed in the processor device in a first processing path comprising an amplification device for amplifying the measurement signal and an analog-to-digital converter for digitizing the measurement signal. The amplification device in particular may be a low-noise amplifier (LNA) for amplifying the measurement signal, in particular a voltage signal, picked up by the at least one sensing electrode. By means of the analog-to-digital converter the (amplified) measurement signal is digitized for the further processing such that the further processing takes place on a digitized version of the measurement signal.

In another aspect, the processor device may be constituted to determine, based on the measurement signal, a correlate of the brain blood volume according to an area obtained from integration of the measurement signal. In particular, the measurement signal, in particular the voltage curve, may be integrated over the opening period of the aortic valve, which can be derived from the measurement signal. In this regard it is to be noted that the measurement signal will be varying and will be roughly periodic with the heart rate. The measurement signal hence can be divided into portions, each portion corresponding to the voltage signal over one heartbeat of the patient. Within such portion the opening period of the aortic valve can be derived, wherein the start point of the opening period can be defined for example by an increase in the voltage signal in the 5 to 15% range. The end point of the opening period of the aortic valve can then be defined as the point in time for which the voltage signal is approaching that same threshold.

Having obtained the correlate of the brain blood volume (which is the area obtained from integration), a correlate for the brain blood flow can be obtained by multiplying said correlate of the brain blood volume with the heart rate. The heart rate can be derived from the measurement signal itself by determining the periodicity of the measurement signal. In particular, the heart rate can be assumed to equal the interval between successive peaks in the voltage signal. By multiplying the correlate of the brain blood volume with the heart rate, a correlate for the brain blood flow is obtained, i.e., a correlate of the blood volume that reaches the patient's brain per minute (so-called cerebral blood flow).

The correlate of the brain blood volume and the correlate of the brain blood flow are correlated to the actual brain blood volume respectively the actual brain blood flow and hence allow to obtain an estimate of the actual brain blood volume and brain blood flow. The actual values of the brain blood volume and brain blood flow may be obtained, according to another aspect of the invention, by using a first non-linear model into which the correlate of the brain blood volume and the brain blood flow are fed to obtain output values indicative of estimates of the actual brain blood volume and the brain blood flow.

The first non-linear model may for example be a fuzzy logic model or a quadratic equation model, which may be trained, in an initial phase, according to training data for which the cerebral blood flow is known. Within the training phase the parameters of the model are defined in a way that the model, being fed with the correlate of the brain blood volume and the brain blood flow, provide for an (accurate) estimate of the actual values of the brain blood volume and the brain blood flow.

The first non-linear model may be fed with further inputs, for example a maximum derivative value of the measurement signal, a maximum positive amplitude of the measurement signal, and maximum negative amplitude of the measurement signal, and/or a value of the left ventricular ejection time derived from the measurement signal. Such features may be derived from the measurement signal itself, in particular from a portion of the measurement signal relating to one heartbeat, such that, by using the first non-linear model, actual values for the brain blood volume and the brain blood flow for each heartbeat are obtained.

In order to for example determine, in addition, an output value indicative of a depth of anesthesia, the output values obtained from the first non-linear model may further be fed into a second non-linear model, which again may be a fuzzy logic model or a quadratic equation model. By means of the second non-linear model, features derived from an EEG signal may be combined with the estimates of the brain blood volume and the brain blood flow obtained from the first non-linear model. Such features may be obtained via a second processing path of the processor device in which an EEG signal is received and processed, for example by deriving features according to symbolic dynamics of the EEG signal, by determining frequency bins of the EEG signal, by determining an entropy value of the EEG signal, and/or by determining a value indicative of burst suppression in the EEG signal.

To obtain the EEG signal, EEG electrodes may be placed on the scalp of the patient's head to pick up a spontaneous electrical activity of the brain of the patient.

The term "electroencephalography (EEG)" generally refers to the recording of electrical activity along the scalp. EEG measures voltage fluctuations resulting from ionic current flows within the neurons of the brain. In clinical contexts, EEG refers to the recording of the brain's spontaneous electrical activity as recorded from multiple electrodes placed on the scalp. Diagnostic applications generally focus on the spectral content of EEG, that is, the type of neural oscillations that can be observed in EEG signals.

The processing of the EEG involves a spectral analysis of the EEG. From the spectrum frequency bins can be defined, relating for example to the energy contents in spectrum portions of 1-4 Hz, 4-8 Hz, 8-12 Hz, 12-20 Hz, 20-45 Hz etc.

Symbolic dynamics may be used to assess the complexity of the EEG. The symbols could be 1 and 0, for example 1 when the EEG is positive and 0 when the EEG is negative. Or the symbols could be designed according to whether the difference between successive samples is larger or smaller than a factor multiplied to the standard deviation of the EEG samples over a given time window. In general, a decrease in the mean or spectral edge frequency of the EEG is occurring when the blood flow is decreased.

Burst suppression of the EEG is characterized by periods of bursts followed by flat EEG, typically occurring during low brain activity caused by anaesthetics, hypoxia or low brain blood flow.

For the analysis of EEG signals, for example a Fast Fourier Transformation (FFT) algorithm may be employed. Using a Fast Fourier Transform algorithm a discrete Fourier transform (DFT) and its inverse may be computed. A Fourier transform converts time (or space) to frequency and vice versa.

In addition, according to another aspect further parameters may be fed into the second non-linear model, for example information relating to a drug infused into the patient, and/or information relating to the patient's weight, height, gender, and/or age or other demographic data relating to the patient.

Within the second non-linear model, the different input data is combined to obtain final values for the estimates of the brain blood volume, the brain blood flow and in particular also an index for the depth of anesthesia. The second non-linear model may be trained, in an initial training phase, using training data for which for example the cerebral blood flow is known and potentially also information relating to the depth of anesthesia is available.

The object is also achieved by a method for estimating the brain blood volume and/or brain blood flow and/or depth of anesthesia of a patient, the method comprising:
  applying an excitation signal using at least one excitation electrode placed on the head of a patient,
  sensing a measurement signal caused by the excitation signal using at least one sensing electrode placed on the head of the patient, and
  processing, using a processor device, said measurement signal sensed by the at least one sensing electrode for determining an output indicative of the brain blood volume and/or the brain blood flow,
wherein, using said processor device, noise in the measurement signal is reduced by applying a non-linear noise-reduction algorithm, in particular using a Poincaré map analysis.

The advantages and advantageous embodiments described above for the system equally apply also to the method.

The idea underlying the invention shall subsequently be described in more detail by referring to the embodiments shown in the figures. Herein:

FIG. 2 shows the placement of EEG electrodes on the scalp of a patient;

FIG. 3A, 3B show the placement of excitation electrodes and sensing electrodes for bio-impedance measurements on the temples of a patient;

FIG. 5A shows a portion of the measurement signal relating to the voltage signal over one heartbeat;

FIG. 5B shows the derivative of a portion of the measurement signal relating to the voltage signal over one heartbeat;

FIG. 7 shows a schematic drawing of a first non-linear model and a second non-linear model for deriving the brain blood volume, the brain blood flow and an index of depth of anesthesia.

Figure 1:
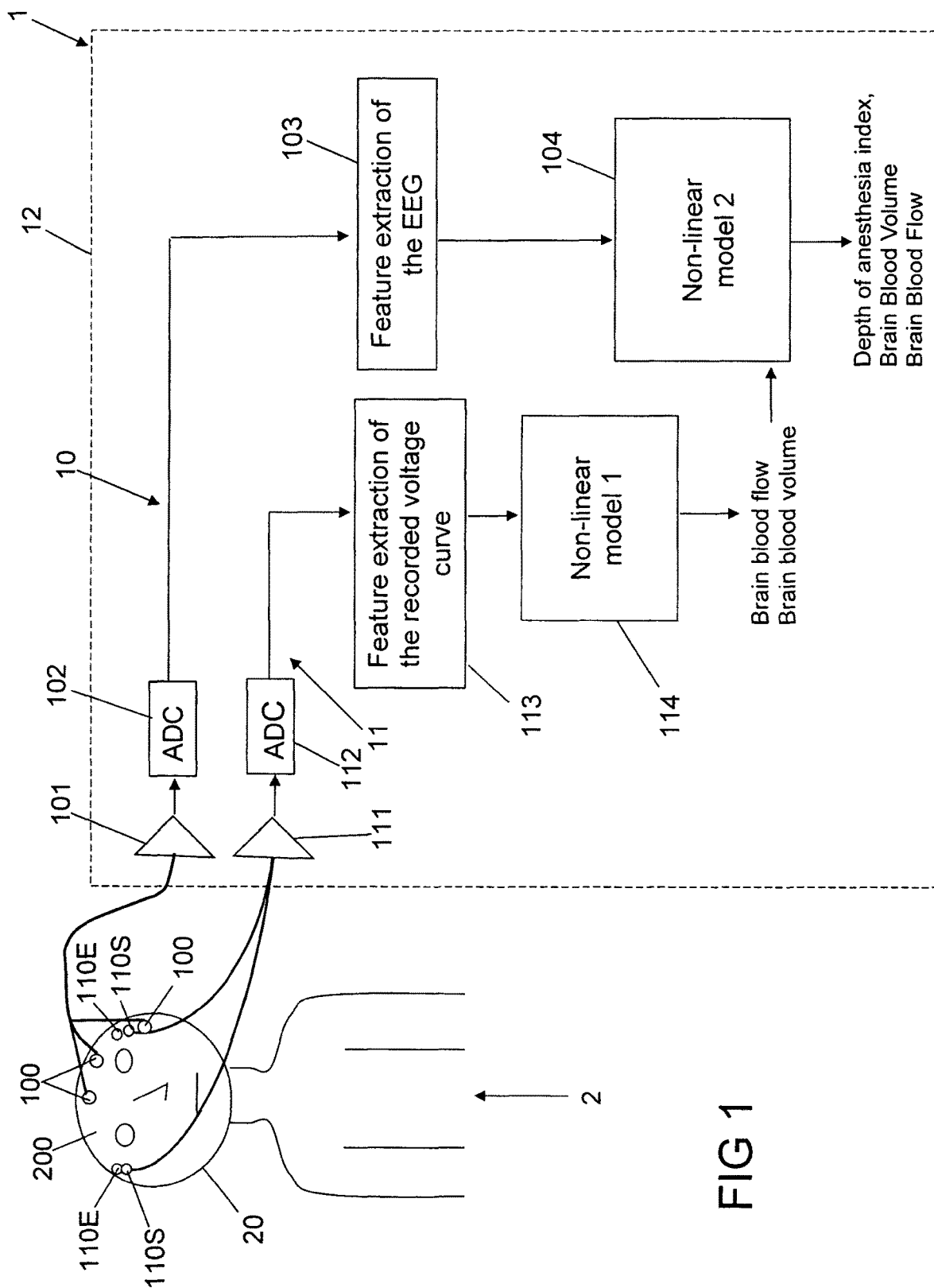
FIG. 1 shows a schematic chart of a system for estimating the brain blood volume, brain blood flow, and/or an index of depth of anesthesia of a patient.

FIG. 1, in a schematic drawing, shows a system 1 for determining estimate values for the brain blood volume and the brain blood flow and also of a depth of anesthesia index of a patient 2.

Within the system 1, different types of signals are combined in a processor device 12 making use of different non-linear models 104, 114 in order to derive, from the input values, output values relating to the brain blood volume, the brain blood flow and the depth of anesthesia index.

The system 1 may be constituted as a computing device, for example a work station. The different units of the processor device 12 herein may be implemented by one or multiple hardware units or by software.

Within the system 1, in particular information derived from a measurement signal obtained from bio-impedance measurements and information obtained from an EEG signal are combined. For this, the processor device 12 comprises different processing paths 10, 11, in which EEG signals (processing path 10) and bio-impedance measurement signals (processing path 11) are processed and, in the non-linear models 104, 114, combined with each other.

For the EEG measurements, electrodes 100 are placed on the scalp 200 of the head 20 of the patient 2, as it is indicated for example in FIG. 2. By means of the electrodes 100, signals relating to be spontaneous brain activity of the patient 2 are picked up and amplified in an amplification unit 101 (in particular a low-noise amplifier) of the processing path 10, after which the amplified EEG signal is fed into an analog-to-digital converter 102 for digitizing the EEG signal.

For the bio-impedance measurements, excitation electrodes 110E and sensing electrodes 110S are placed on the temples of the head 20 of the patient 2, as it is shown by way of example in FIGS. 3A and 3B. One excitation electrode 110E herein is placed on each temple of the patient's head 20, and an excitation signal in the shape of a constant current at an elevated frequency is injected in between the excitation electrodes 110E to flow through the patient's head. The excitation current may for example have a (constant) amplitude in the range between 50 and 1000 µA. By the excitation current, which seeks its path through the patient's head 20 in particular along the blood-filled arteries within the patient's head 20, a voltage signal is caused which is linked to the injected current via the bio-impedance. This voltage signal is picked up by the two sensing electrodes 110S, each sensing electrode 110S being arranged in the vicinity of an excitation electrode 110E, as it is shown in FIGS. 3A and 3B.

The measurement signal picked up via the sensing electrodes 110S is fed into an amplification unit 111 of the processing path 11, in particular a low-noise amplifier, in which it is amplified and further fed to an analog-to-digital converter 112 for digitizing the measurement signal.

Figure 4A:
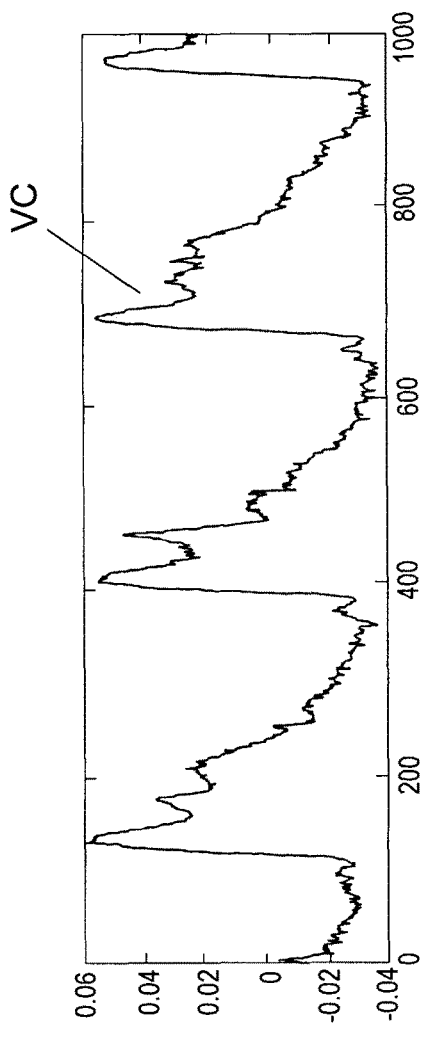
FIG. 4A shows a measurement signal in the shape of a voltage signal (voltage curve)

The measurement signal in the shape of a voltage curve VC is shown in an example in FIG. 4A. The voltage curve VC is achieved for each heartbeat, wherein voltage curves VC for consecutive heartbeats usually have a similar morphology.

Figure 4C:
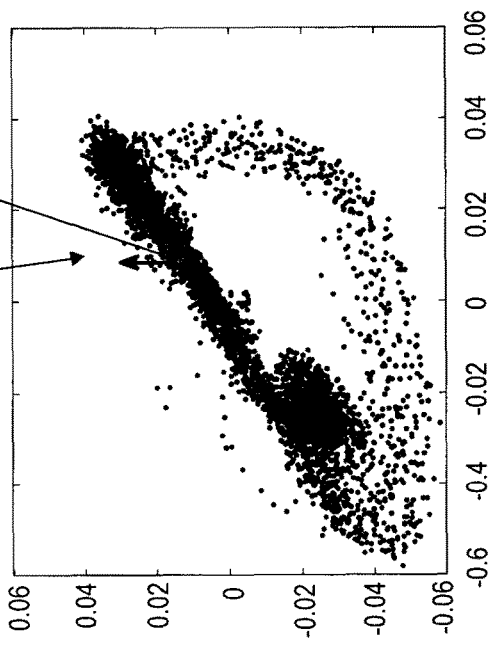
FIG. 4C shows the Poincaré map indicating a neighbourhood within the Poincaré map.
Figure 4B:
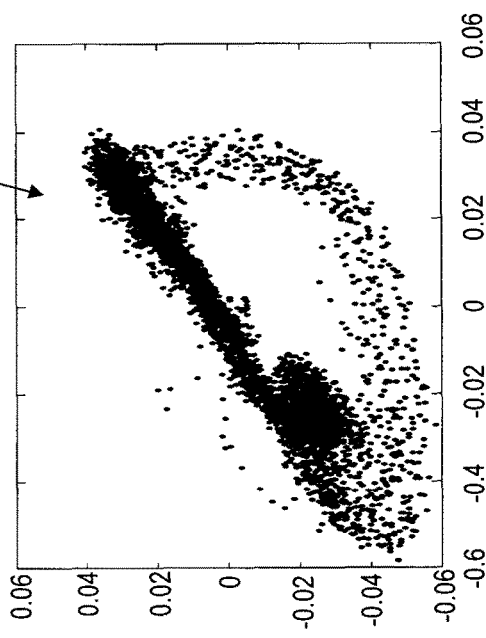
FIG. 4B shows a Poincaré map relating to the measurement signal.

For the processing of the voltage curve VC, a noise removal algorithm is applied to the digitized signal which is based on Poincaré maps for the underlying patterns to emerge from a noisy signal. In one embodiment, noise is reduced by applying a Poincaré map analysis, in which a Poincaré map M as shown in FIG. 4B is formed by plotting the voltage curve VC over a delayed version of the voltage curve VC. Due to the digitization of the measurement signal, discrete points arise which can be assumed to tend towards a so-called attractor.

Generally, chaotic signals are deterministic signals with embedded irregular patterns. Most of the physiological electrical signals are controlled by several underlying biological processes and therefore present this kind of behaviour. An attractor is the geometric set of points to which a chaotic signal will tend to even though initial conditions are slightly modified. One of the most commonly used methods to study attractors is the method of delayed coordinates, in which each dimension of the attractor corresponds to the original time series delayed by a certain delay.

Given the time series $$x=[x_1 x_2 x_3 \ldots x_{n-1} x_n]$$

where $$x_i = x(t=i),$$

its attractor with a time lag τ and embedding dimension m is defined as:

$$A=[x(t)x(t+\tau) \ldots x(t+(m-2)\tau)x(t+(m-1)\tau)]$$

in which each column corresponds to a version delayed by τ with respect to the previous time series.

Considering for example an attractor with time lag τ=1 and embedding dimension m=2, it will be defined by the equation:

$$A=[x(t)x(t+1)]$$

and its state-space representation, the so called Poincaré map, is obtained by plotting one coordinate of A as a function of the other.

Figure 4D:
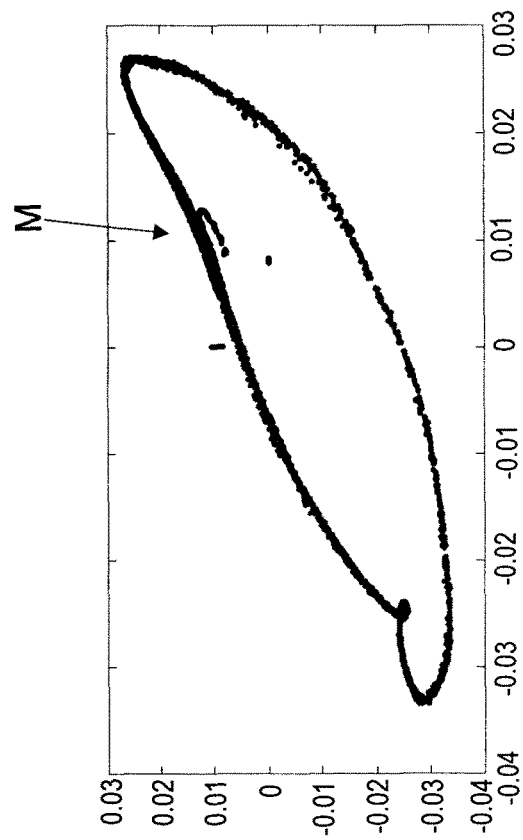
FIG. 4D shows the Poincaré map after projecting points to the new coordinates system obtained by disregarding coordinates having a reduced contribution to the variance of the measurement signal.

Within a Poincaré map, neighbourhoods N can be identified by clustering points: points are randomly selected and for each selected point its neighbourhood N is defined as the group of v closest points. This procedure is repeated until all points in the map belong to a neighbourhood N. For each neighbourhood N, a new coordinate system is defined, centered in its gravity center, and new coordinates are computed for each point in the neighborhood N. From the set of coordinates computed, the ones providing for a low amount of variance of the total neighbourhood N are removed and coordinates of each point are recalculated for the new space with reduced dimension. By disregarding those dimensions which have a reduced contribution to the variance of the measurement signal and which hence can be assumed to be due to noise, only those coordinates remain which have a substantial contribution to the variance. Afterwards, all points in the neighbourhood N are projected into the new coordinate system, with dimension smaller than M, and the resulting Poincaré plot is obtained, as it is shown in FIG. 4D.

Figure 4E:
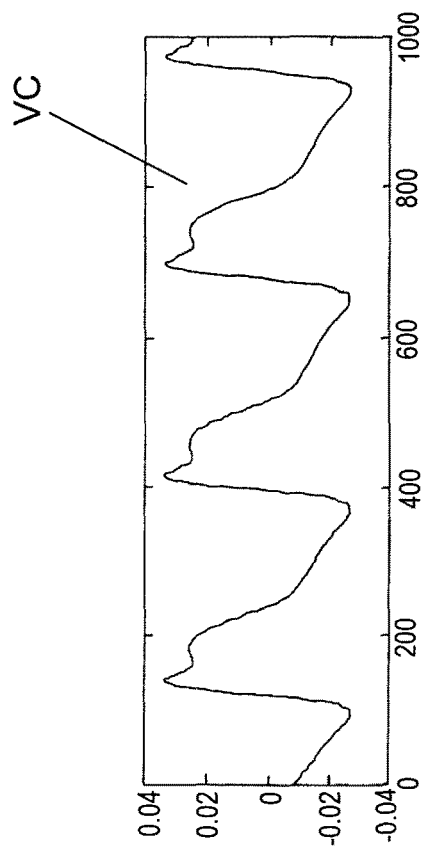
FIG. 4E shows a reconstructed, noise-reduced version of the measurement signal.

By reconstructing the measurement signal in the shape of the voltage curve VC, then, a noise-reduced version of the measurement signal in the shape of the voltage curve VC is obtained, as shown in FIG. 4E.

It is to be noted that a single Poincaré map with m dimensions exists, each dimension corresponding to a different time lag. Therefore, the analysis is performed on a single m-dimensional map. A drawing of a 2D map is illustrated in FIGS. 4B and 4C for simplicity, as an m dimensional map cannot be visually presented. The noise removal however is applied to a single m-dimensional map.

Furthermore, the process including the above steps may iteratively be repeated. The algorithm hence may again be applied to the reconstructed signal in order to further reduce noise, until a noise reduction considered sufficient for a further processing is obtained.

Poincaré map analysis is for example described by R. Cawley and G.-H. Hsu in "Local-geometric-projection method for noise reduction in chaotic maps and flows", Physical Review A, Col. 46, No. 6, 1992, pages 3057 to 3082, whose contents shall be incorporated by reference herein.

The further processing now can take place on the noise-reduced version of the measurement signal in the shape of the voltage curve VC, as shown in FIG. 4E.

In particular, from a portion of the voltage curve VC relating to one heartbeat as shown in FIG. 5A, features such as a maximum slope dV/dt, a maximum positive amplitude maxHpos and a maximum negative amplitude maxHneg can be derived (block 113 in FIG. 1).

From the derivative DVC of the voltage curve VC, as shown in FIG. 5B, furthermore the left ventricular ejection time LVET can be estimated as the period from a point B, defined as the minimum of the DVC prior to the maximum point C, to a point X, defined as the minimum of the DVC immediately after said point C.

In addition, by integrating the voltage curve VC over the LVET period an area A is obtained which is a correlate to the brain blood volume.

Figure 6A:
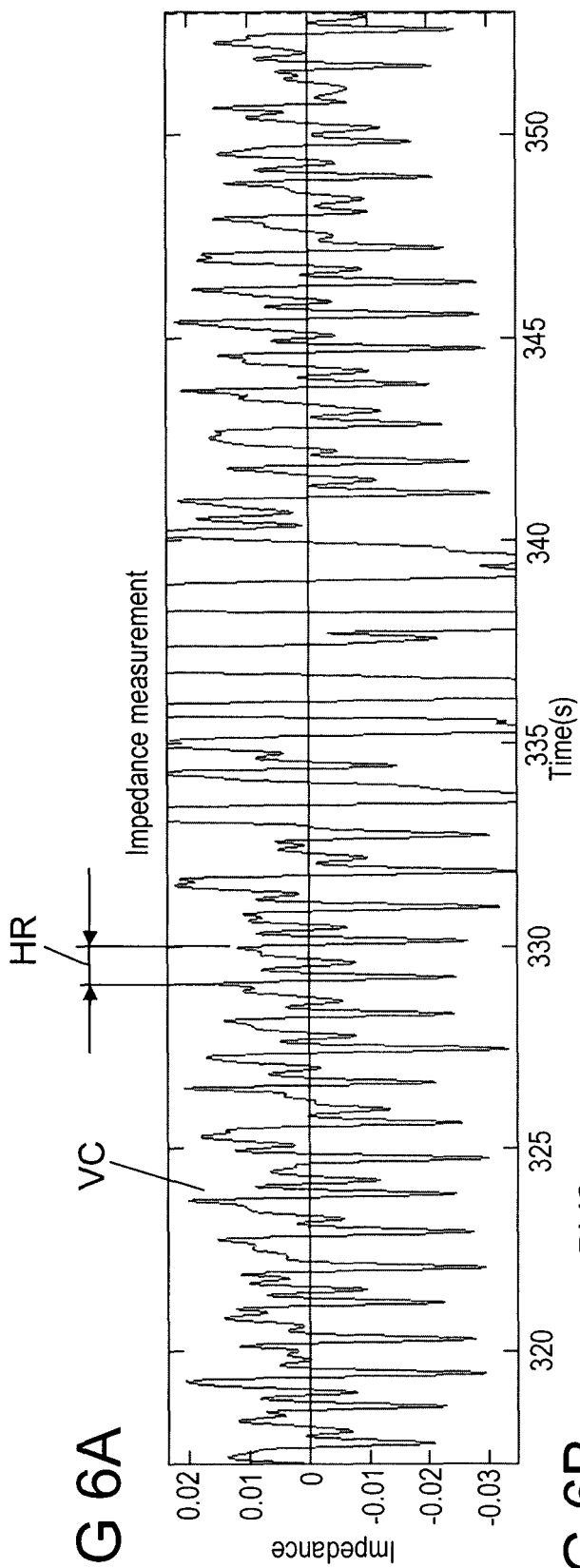
FIG. 6A shows a measurement signal over time.
Figure 6B:
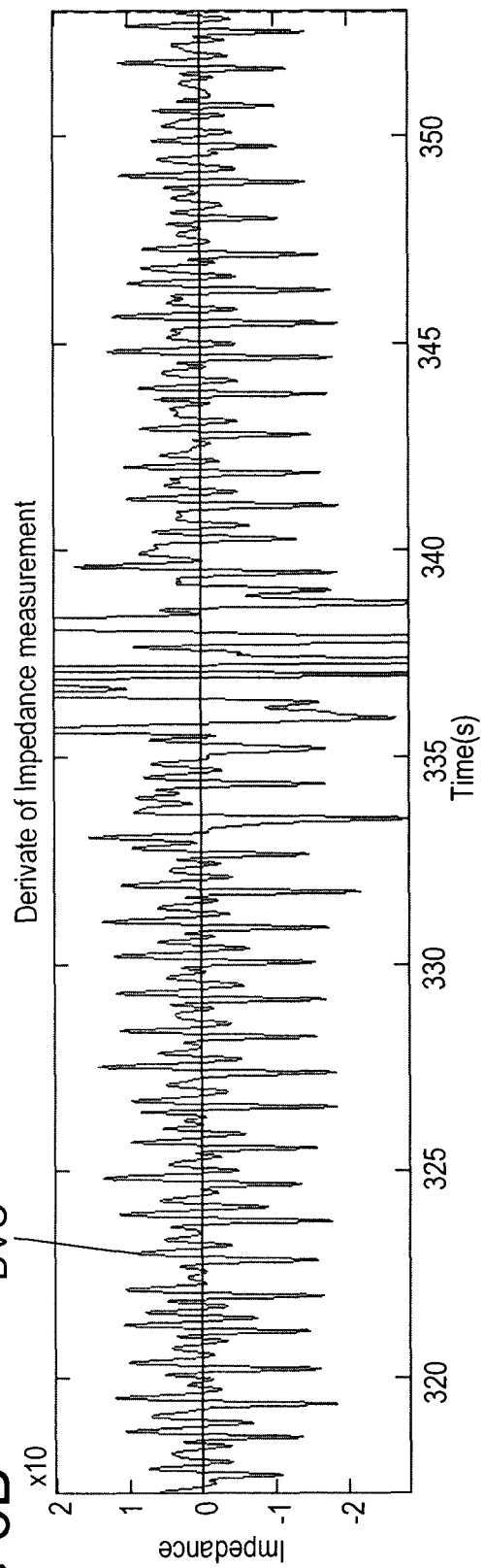
FIG. 6B shows the derivative of the measurement signal of FIG. 6A.

From the correlate of the brain blood volume, also a correlate of the brain blood flow can be derived. From the periodicity of the voltage curve VC, the heart rate HR can be detected, is indicated for example in FIG. 6A. By multiplying the heart rate with the brain blood volume (BV), the correlate of the brain blood flow (BF) is obtained as $$BF = HR \times BV.$$

The parameters extracted from the voltage curve VC and the correlate of the brain blood volume and the brain blood flow are fed as inputs to the first non-linear model 114, as this is shown in FIG. 7. The first non-linear model 114 may for example be a fuzzy logic model or a quadratic equation model, which combines the features and outputs estimates of the actual brain blood volume and the actual brain blood flow.

As shown in FIGS. 1 and 7, the output of the first non-linear model 114 is fed, together with other parameters, to the second non-linear model 104. The second non-linear model 104 takes, as further inputs, features derived from the EEG signal and further demographic information about the patient 2 such as the patient's height, weight, gender and age and further information relating to drugs infused to the patient 2.

Within the processing path 10, features are extracted from the EEG signal in block 103 (see FIG. 1). In particular, frequency bins can be defined relating to the energy in spectrum portions for example between 1 to 4 Hz, 4 to 8 Hz, 8 to 12 Hz, 12 to 20 Hz and 20 to 45 Hz, etc. Symbolic dynamics can be used to assess the complexity of the EEG signal, for example employing symbols 1 and 0 for positive portions of the EEG signal respectively negative portions of the EEG signal. Information relating to a burst suppression may be derived, characterized by portions of bursts followed by flat portions within the EEG signal.

Within the second non-linear model 104, which like the first non-linear model 114 may for example be a fuzzy logic model or a quadratic equation model, the different parameters are combined with each other to output a final estimate of the brain blood volume and the brain blood flow, and also an estimate of a depth of anesthesia index.

The second model 104 aims at exploring the causal relationship between cerebral blood flow and EEG activity, and integrates information from both in order to output final indices of the brain blood volume and brain blood flow that take into account current EEG activity, as well as a depth of anesthesia index that considers blood flow in its algorithm.

Both models 104, 114 may take more or less inputs than described above.

The training of the non-linear models is beneficially carried out with a large amount of data where the cerebral blood flow is known for the patient. The training defines the parameters of the models which can then predict the cerebral blood flow when the inputs are presented to the model.

As said, for the processing non-linear models in the shape of fuzzy logic models or quadratic equation models may be employed. However, also other non-linear models may be used.

In the following, by way of example details about ANFIS models and quadratic equation models are provided.

ANFIS Model:

A fuzzy logic model may for example be the so-called ANFIS model. In that case, the system 1 uses ANFIS models to combine the parameters, for the definition of the blood volume, cerebral blood flow and the depth of anesthesia index. The parameters extracted from the cerebral impedance and the EEG signals and the demographic data of the patient are used as input to an Adaptive Neuro Fuzzy Inference System (ANFIS).

ANFIS is a hybrid between a fuzzy logic system and a neural network. ANFIS does not assume any mathematical function governing the relationship between input and output. ANFIS applies a data driven approach where the training data decides the behaviour of the system.

Figure 8A:
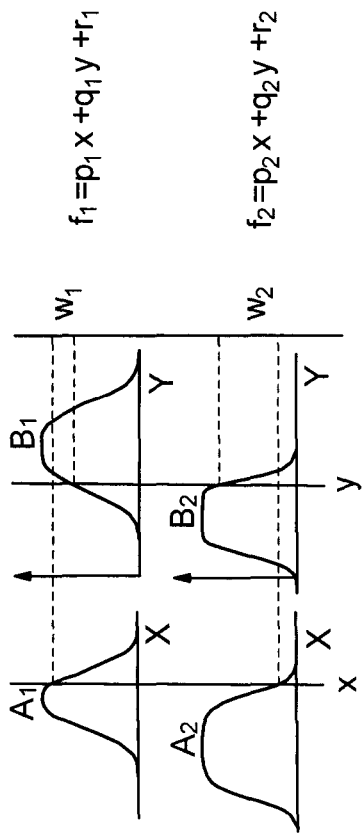
FIG. 8A, 8B show a mathematical formulation of an ANFIS non-linear model.
Figure 8B:
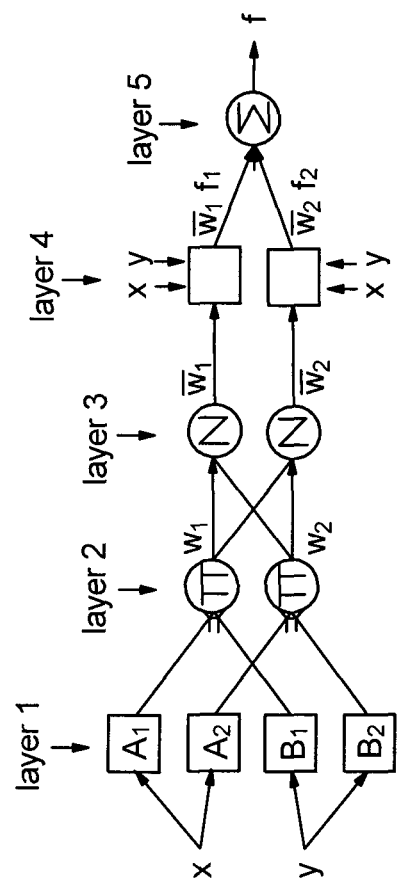

The five layers of ANFIS, shown in FIGS. 8A and 8B, have the following functions:

Each unit in Layer 1 stores three parameters to define a bell-shaped membership function. Each unit is connected to exactly one input unit and computes the membership degree of the input value obtained.

Each rule is represented by one unit in Layer 2. Each unit is connected to those units in the previous layer, which are from the antecedent of the rule. The inputs into a unit are degrees of membership, which are multiplied to determine the degree of fulfilment for the rule represented.

In Layer 3, for each rule there is a unit that computes its relative degree of fulfilment by means of a normalisation equation. Each unit is connected to all the rule units in Layer 2.

The units of Layer 4 are connected to all input units and to exactly one unit in Layer 3. Each unit computes the output of a rule.

An output unit in Layer 5 computes the final output by summing all the outputs from Layer 4.

Standard learning procedures from neural network theory are applied in ANFIS. Back-propagation is used to learn the antecedent parameters, i.e. the membership functions, and least squares estimation is used to determine the coefficients of the linear combinations in the rules' consequents. A step in the learning procedure has two passes. In the first pass, the forward pass, the input patterns are propagated, and the optimal consequent parameters are estimated by an iterative least mean squares procedure, while the antecedent parameters are fixed for the current cycle through the training set. In the second pass (the backward pass) the patterns are propagated again, and in this pass back-propagation is used to modify the antecedent parameters, while the consequent parameters remain fixed. This procedure is then iterated through the desired number of epochs. If the antecedent parameters initially are chosen appropriately, based on expert knowledge, one epoch is often sufficient as the LMS algorithm determines the optimal consequent parameters in one pass and if the antecedents do not change significantly by use of the gradient descent method, neither will the LMS calculation of the consequents lead to another result. For example in a 2-input, 2-rule system, rule 1 is defined by if $x$ is $A$ and $y$ is $B$ then $f_1 = p_1 x + q_1 y + r_1$ where p, q and r are linear, termed consequent parameters or only consequents. Most common is f of first order as higher order Sugeno fuzzy models introduce great complexity with little obvious merit.

The inputs to the ANFIS system are fuzzified into a number of predetermined classes. The number of classes should be larger or equal two. The number of classes can be determined by different methods. In traditional fuzzy logic the classes are defined by an expert. The method can only be applied if it is evident to the expert where the landmarks between two classes can be placed. ANFIS optimizes the position of the landmarks, however the gradient descent method will reach its minimum faster if the initial value of the parameters defining the classes is close to the optimal values. By default, ANFIS initial landmarks are chosen by dividing the interval from minimum to maximum of all data into n equidistant intervals, where n is the number of classes. The number of classes could also be chosen by plotting the data in a histogram and visually deciding for an adequate number of classes, by ranking as done by FIR, through various clustering methods or Markov models. The ANFIS default was chosen for this invention and it showed that more than three classes resulted in instabilities during the validation phase, hence either two or three classes were used.

Both the number of classes and number of inputs add to the complexity of the model, i.e., the number of parameters. For example, in a system with four inputs each input may be fuzzified into three classes consisting of 36 antecedent (non-linear) and 405 consequent (linear) parameters, calculated by the following two formulas:

antecedents=number of classes×number of inputs×3 consequents=number of classes number of inputs×
(number of inputs+1)

The number of input-output pairs should in general be much larger (at least a factor 10) than the number of parameters in order to obtain a meaningful solution of the parameters.

A useful tool for ensuring stability is the experience obtained by working with a certain neuro-fuzzy system such as ANFIS in the context of a particular data set, and testing with extreme data for example obtained by simulation ANFIS uses a Root Mean Square Error (RMSE) to validate the training result and from a set of validation data the RMSE validation error can be calculated after each training epoch. One epoch is defined as one update of both the antecedent and the consequent parameters. An increased number of epochs will in general decrease the training error.

Quadratic Model

Alternatively, quadrative equation models may be used for the models 104, 114. In that case, the system 1 uses quadratic models to combine the parameters for the definition of the blood volume, cerebral blood flow and the depth of anesthesia index. The parameters extracted from the cerebral impedance and the EEG signals and the demographic data of the patient are used as inputs to a quadratic model.

The output indexes are derived from quadratic generalized models that use as inputs data extracted from the EEG, cerebral impedance and demographic patient data. Such a model contains an independent coefficient called Intercept, one linear term per input, a square term per input and interaction terms between each pair of entries. The model can be expressed as:

$$\text{Output} = \text{Intercept} + \sum_{i=1}^{n} a_i * Input_i + \sum_{i=1}^{n} b_i * Input_i^2 + \sum_{j=1}^{n} \sum_{i=j+1}^{n} c_{j,i} * Input_i * Input_j$$

Where:
Intercept: intersection or constant term.
Input: input model.
Output: model output.
n: number of model inputs
a: linear terms.
b: square terms.
c: interaction terms between inputs.

LIST OF REFERENCE NUMERALS

1 System
10 EEG processing path
100 Electrodes
101 Amplification device
102 Analog-digital converter
103 Feature extraction unit
104 Model unit
11 EEG processing path
110E Excitation electrode
110S Sensing electrode
111 Amplification device
112 Analog-digital converter
113 Feature extraction unit
114 Model unit
12 Processor device
2 Patient
20 Head
200 Scalp
A Area
DVC Derivative of voltage curve
M Poincaré map
N Neighbourhood
VC Measurement signal (Voltage curve)

The invention claimed is:
1. A system for estimating the brain blood volume and/or brain blood flow and/or depth of anesthesia of a patient, comprising:
at least one excitation electrode to be placed on a temple of the head of a patient for applying an excitation signal, at least one sensing electrode to be placed on the other temple of the head of the patient for sensing a measurement signal (VC) caused by the excitation signal, at least one electrode to be placed on the scalp of the patient's head to receive an EEG signal of spontaneous electrical activity of the brain of the patient, and a processor device for processing said measurement signal (VC) sensed by the at least one sensing electrode for determining an output indicative of the brain blood volume and/or the brain blood flow, said measurement signal (VC) being processed in the processor device in a first processing path comprising an amplification device for amplifying the measurement signal (VC) and an analog-to-digital converter for digitizing the measurement signal (VC), and said EEG signal received by the at least one EEG electrode being processed in the processor device in a second processing path for receiving and processing the EEG signal, wherein the processor device is constituted to reduce noise in the measurement signal (VC) by applying a non-linear noise-reduction algorithm based on a Poincare map analysis, and wherein the processor device is constituted to determine, based on the noise-reduced version of the measurement signal (VC), a correlate of the brain blood volume according to an area (A) obtained from integration of the measurement signal (VC), and wherein the area (A) is obtained from integration of the measurement signal (VC) over the left ventricular ejection time (LVET), which is estimated as the period from a point (B), defined as the minimum of the derivative of the measurement signal (VC) prior to a maximum point (C), to a point (X), defined as the minimum of the derivative of the measurement signal (VC) immediately after said maximum point (C), and wherein the processor device is further constituted (i) to determine a correlate of the brain blood flow by multiplying said correlate of the brain blood volume with a value indicative of the heart rate of the patient, (ii) to feed the correlate of the brain blood volume and/or the correlate of the brain blood flow into a first non-linear model comprising a fuzzy logic model or a quadratic equation model, to obtain output values indicative of the brain blood volume and/or the brain blood flow, and (iii) to feed features derived from the EEG signal and said output values into a second non-linear model to obtain final output values for the brain blood volume and/or the brain blood flow, and/or an output value indicative of a depth of anaesthesia.

2. The system according to claim 1, wherein the at least one excitation electrode is controlled to inject an electrical current having one or more predetermined frequencies and/or having a constant amplitude.

3. The system according to claim 1, wherein the processor device is constituted to derive said value indicative of the heart rate from the measurement signal (VC).

4. The system according to claim 1, wherein the processor device in constituted to feed, as further inputs, at least one of the group of a maximum derivative value of the measurement signal (VC), a maximum positive amplitude of the measurement signal (VC), a maximum negative amplitude of the measurement signal (VC), and a value of the left ventricular ejection time (LVET) derived from the measurement signal (VC) into the first non-linear model.

5. The system according to claim 1, wherein said features of the EEG signal are derived according to symbolic dynamics of the EEG signal, by determining frequency bins of the EEG signal, by determining an entropy value of the EEG signal, and/or by determining a value indicative of burst suppression in the EEG signal.

6. The system according to claim 1, wherein the processor device is constituted to feed, as further inputs, at least one of the group of information relating to a drug infused into the patient, and information relating to the patient's weight, height, gender, and/or age into the second non-linear model.

7. The system according to claim 1, wherein the second non-linear model is a fuzzy logic model or a quadratic equation model.

8. A method for estimating the brain blood volume and/or brain blood flow and/or depth of anesthesia of a patient, comprising:

applying an excitation signal using at least one excitation electrode placed on a temple of the head of a patient, sensing a measurement signal (VC) caused by the excitation signal using at least one sensing electrode placed on the other temple of the head of the patient, receiving an EEG signal of spontaneous electrical activity of the brain of the patient using at least one electrode placed on the scalp of the patient's head, processing, using a processor device, said measurement signal (VC) sensed by the at least one sensing electrode for determining an output indicative of the brain blood volume and/or the brain blood flow, said processing said measurement signal (VC) being performed in a first processing path comprising an amplification device for amplifying the measurement signal (VC) and an analog-to-digital converter for digitizing the measurement signal (VC), said EEG signal received by the at least one EEG electrode being processed in the processor device in a second processing path for receiving and processing the EEG signal, using said processor device to reduce noise in the measurement signal (VC) by applying a non-linear noise-reduction algorithm based on a Poincare map analysis, wherein further processing takes place on the noise-reduced version of the measurement signal (VC), while based on the noise-reduced version of the measurement signal (VC), a correlate of the brain blood volume according to an area (A) obtained from integration of the measurement signal (VC) is determined, with the area (A) being obtained from integration of the measurement signal (VC) over the left ventricular ejection time (LVET), which is estimated as the period from a point (B), defined as the minimum of the derivative of the measurement signal (VC) prior to a maximum point (C), to a point (X), defined as the minimum of the derivative of the measurement signal (VC) immediately after said maximum point (C), and using the processor device (i) to determine a correlate of the brain blood flow by multiplying said correlate of the brain blood volume with a value indicative of the heart rate of the patient, (ii) to feed the correlate of the brain blood volume and/or the correlate of the brain blood flow into a first non-linear model comprising a fuzzy logic model or a quadratic equation model, and (iii) to feed features derived from the EEG signal and said output values into a second non-liner model to obtain final output values for the brain blood volume and/or the brain blood flow, and or an output value indicative of a depth of anaesthesia.

* * * * *